United States Patent
Lansonneur

(10) Patent No.: US 12,343,562 B2
(45) Date of Patent: Jul. 1, 2025

(54) RADIOTHERAPY DOSE PARAMETER COMPUTATION TECHNIQUES

(71) Applicant: Varian Medical Systems, Inc., Palo Alto, CA (US)

(72) Inventor: Pierre Lansonneur, Lyons (FR)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 512 days.

(21) Appl. No.: 17/882,452

(22) Filed: Aug. 5, 2022

(65) Prior Publication Data
US 2024/0042236 A1    Feb. 8, 2024

(51) Int. Cl.
*A61N 5/10*        (2006.01)
(52) U.S. Cl.
CPC .................................. *A61N 5/1031* (2013.01)
(58) Field of Classification Search
CPC .................................................... A61N 5/1031
See application file for complete search history.

(56) References Cited

U.S. PATENT DOCUMENTS

| | | |
|---|---|---|
| 2011/0122997 A1 | 5/2011 | Lu et al. |
| 2020/0306559 A1 | 10/2020 | Kuusela et al. |
| 2021/0268313 A1 | 9/2021 | Gunnarsson et al. |
| 2022/0126117 A1 | 4/2022 | Voronenko et al. |

FOREIGN PATENT DOCUMENTS

WO    WO-2021/036366    3/2021

*Primary Examiner* — Nicole M Ippolito
*Assistant Examiner* — Hanway Chang
(74) *Attorney, Agent, or Firm* — Harness, Dickey & Pierce, P.L.C.

(57) ABSTRACT

Radiotherapy dose computation techniques including receiving a set of spot locations and corresponding spot weights. The set of spot locations and corresponding spot weights can be interpolated as a function of two coordinate location parameters (x, y) or three coordinate location parameters (x, y, α). An objective function of the interpolated spot locations and corresponding spot weights can also be computed. Interpolating the spot locations and the corresponding spot weights and computing of the objective function can be performed until the objective function converges to obtain optimized spot dose parameters.

20 Claims, 8 Drawing Sheets

RADIOTHERAPY DOSE PARAMETER COMPUTATION TECHNIQUES

BACKGROUND OF THE INVENTION

Radiotherapy can be used in the treatment of cancer, tumors, lesion, and the like. Radiotherapy involves directing a beam of high energy radiation, such as but not limited to charged particles, (e.g., ions), protons, electrons, or photons (e.g., x-ray, Gamma), into a target volume. One of the goals of radiotherapy treatment is to maximize the dose supplied to a target, such as a tumor, while minimizing the dose absorbed by the surrounding tissue. A treatment plan is used to specify various aspects of the radiotherapy to deliver sufficient radiation to unhealthy tissue in a planned target volume (PTV), while minimizing exposure of surrounding healthy tissue.

In a number of radiotherapy systems, treatment parameters include doses for a set of fixed spot locations. For example, the treatment parameters can specify dose weights for individual spots located on a fixed lattice (e.g., hexagonal or rectilinear). To fulfill dosimetric constraints the dose can be optimized over the fixed locations. For a set of N spots with fixed position, the dose in a voxel i can be written as a matrix product of a spot dose influence matrix (IM) and spot weights (W) according to Equation 1:

$$D_i(W) = \Sigma_{j=1}^{N} W_j \cdot IM_{ij} \quad (1)$$

The goal of optimizing spot weights at fixed locations is to minimize a so-called objective function $f$ that is a function of the dose D. An important quantity for such an optimization problem is the gradient of the object function $\nabla f$, that can be written as a function of the spot dose influence matrix according to Equation 2:

$$\nabla f = \frac{\partial f}{\partial W_j} = \frac{\partial f}{\partial D_i} \cdot \frac{\partial D_i}{\partial W_j} = \frac{\partial f}{\partial D_i} \cdot IM_{ij} \quad (2)$$

where $$\frac{\partial f}{\partial D_i}$$

can be calculated using methods such as nearest neighbor interpolation.

The conventional optimization of dose treatment parameters however can still result in sub-optimal results. The dose parameters can be sub-optimal when the range of the spot weights is limited. The optimization may also be sub-optimal for use cases such as overcoming machine hardware constraints, increasing the dose rate (e.g., Ultra-High Dose Rate Radiotherapy (FLASH-RT)), reducing the number of spots in the treatment plan, and reducing the delivery time. Accordingly, there is a continuing need for improved radiotherapy parameter optimization techniques.

SUMMARY OF THE INVENTION

The present technology may best be understood by referring to the following description and accompanying drawings that are used to illustrate embodiments of the present technology directed toward radiotherapy dose parameter computation techniques.

In one embodiment, a radiotherapy dose computation method can include receiving an initial set of spot locations and initial corresponding spot weights. A spot dose influence matrix of the initial spot locations and corresponding spot weights can be computed. The spot locations and corresponding spot weights can be interpolated as a function of two coordinate location parameters (x, y), or three coordinate location parameters (x, y, α). An objective function can be computed for the interpolated spot locations and corresponding spot weights A gradient of the objective function can also be computed. The interpolated spot locations and corresponding spot weights can be adjusted based on the gradient of the objective function. Interpolating the spot locations and corresponding spot weights, computing the objective function, computing the gradient, and adjusting the interpolated spot locations and corresponding spot weights can be iteratively performed until the objective function converges.

In one embodiment, the interpolated spot locations and corresponding spot weights, upon convergence of the objective function, can be utilized to control a radiotherapy delivery system such as, but not limited to, an Intensity Modulated Proton Therapy (IMPT) delivery system, a Proton Modulated Arc Therapy (PMAT) delivery system, a Non-coplanar proton Modulated Arc Therapy (4Pi-PMAT) delivery system, or Ultra-High Dose Rate Radiotherapy (FLASH-RT) delivery system. Dose optimization based on interpolating over both spot weight and spot location can reduce computation workload, as compared to directly computing spot weights and spot locations. Furthermore, dose optimization based on interpolating over both spot weight and spot location can also provide dose optimizations that are as good or better as compared to just interpolating over the spot weights.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Figure 1:
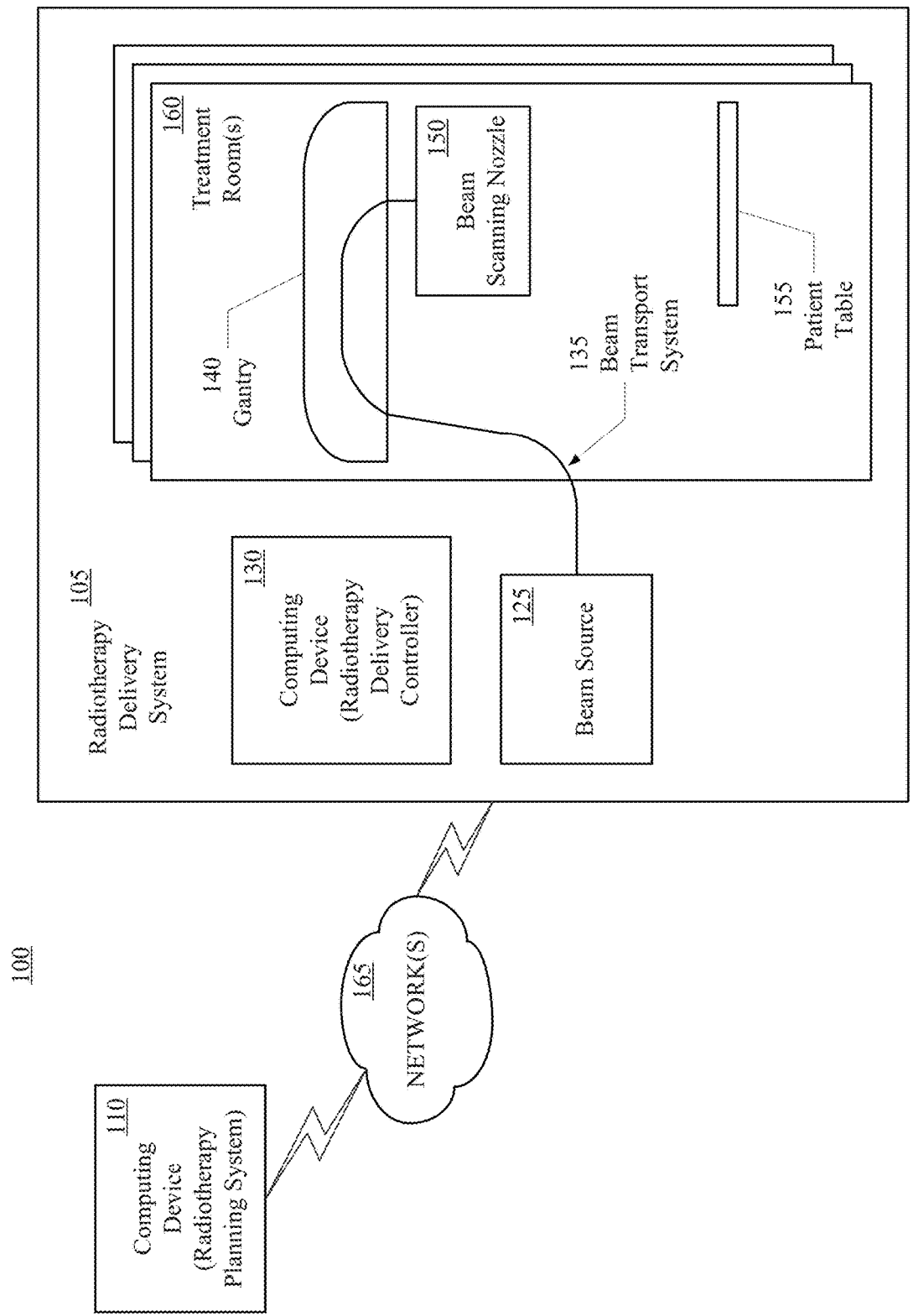
FIG. 1 shows an exemplary radiotherapy system, in accordance with aspects of the present technology.

Reference will now be made in detail to the embodiments of the present technology, examples of which are illustrated in the accompanying drawings. While the present technology will be described in conjunction with these embodiments, it will be understood that they are not intended to limit the technology to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. The use of the terms "comprises," "comprising," "includes," "including" and the like specify the presence of stated elements, but do not preclude the presence or addition of one or more other elements and or groups thereof. It is also to be understood that although the terms first, second, etc. may be used herein to describe various elements, such elements should not be limited by these terms. These terms are used herein to distinguish one element from another. For example, a first element could be termed a second element, and similarly a second element could be termed a first element, without departing from the scope of embodiments. It is also to be understood that when an element is referred to as being "coupled" to another element, it may be directly or indirectly connected to the other element, or an intervening element may be present. In contrast, when an element is referred to as being "directly connected" to another element, there are not intervening elements present. It is also to be understood that the term "and or" includes any and all combinations of one or more of the associated elements. It is also to be understood that the phraseology and terminology used herein is for the purpose of description and should not be regarded as limiting.

Referring to FIG. 1, an exemplary radiotherapy system, in accordance with aspects of the present technology, is shown. The radiotherapy system 100 can include a radiotherapy delivery system 105, and optionally a radiotherapy planning system 110 and/or the like communicatively coupled to the radiotherapy delivery system 105. The radiotherapy delivery system 105 can include, but is not limited to, a beam source 125, one or more radiotherapy delivery controllers 130 and one or more beam transport systems 135. The radiotherapy delivery system 105 can further include a gantry 140, beam scanning nozzle 150 and a patient table 155 disposed in each of one or more treatment rooms 160. The beam source 125 can be coupled to the gantry 140 and beam scanning nozzle 150 of the respective treatment room 160 by the beam transport system 135. The beam transport system 135 can be configured to focus and shape energy beams and guide them to the gantries 140 in the one or more treatment rooms 160. The gantry 140 can rotate about the patient on the patient table 155 to deliver the energy beam at any angle while minimizing the need to reposition the patient. The patient table 155 can include a sophisticated patient positioning system that moves in one or more directions to position patients. The beam scanning nozzle 150 can be configured to scan a broad beam, a pencil beam or the like about a target area of the patient.

The one or more radiotherapy delivery controllers 130 can be configured to control the operation of the beam source 125, the beam transport systems 135, the gantries 140, beam scanning nozzles 150 and/or patient tables 155 based on a given patient radiotherapy treatment plan. One or more computing devices 110 can also be configured to generate patient radiotherapy treatment plans for corresponding patients. The one or more computing devices 110, 130 can include one or more processors, one or more memories, one or more network interfaces, and one or more input/output devices, such as keyboards, pointing devices, displays and/or the like, coupled together by one or more busses. The one or more computing devices 110, 130 can be any type of computing device, including but not limited to desktop Personal Computers (PCs), laptop PCs, server computer, virtual machine, cloud computing platform, or the like. The one or more computing devices 110, 130 can be coupled directly to each other, and/or can be coupled through one or more networks 165, including Local Area Networks (LAN), Wide Area Networks (WAN), the Internet or the like.

Alternatively or in addition, one or more of the computing devices 110, 130 can be combined together and/or integral to one or more other subsystems of the radiotherapy system 100.

During treatment, the beam nozzle and/or the patient can be moved relative to one another so that the beam can be directed into the planned target volume (PVT) from different directions (beam geometries). The target may have an irregular shape, and/or the amount (depth) of normal, healthy tissue along the beam path may vary dependent on the beam geometry. In general, it may be necessary to shape the dose distribution delivered by a beam according to the shape and depth of the target and the beam geometry.

In many cases, radiation can be delivered to the target tissue with sub-millimeter precision, while mostly sparing normal tissue, ultimately leading to killing cells in the target tissue. However, the tumor cells' ability to escape the cell killing effects of radiation and/or to develop resistance mechanisms can counteract the cell killing effect of radiotherapy, potentially limiting the therapeutic effect of radiotherapy. Furthermore, delivery of ultra-high dose radiation, in radiotherapy treatment techniques such as Ultra-High Dose Rate Radiotherapy (FLASH-RT) treatment plans, are believed to spare normal tissue from radiation-induced toxicity. Optimization the delivered dose can improve the performance radiotherapy treatment systems, such as Ultra-High Dose Rate Radiotherapy (FLASH-RT). Optimization of the delivered dose can also reduce the number of number of spots in a treatment plan, reduce delivery times, and the like.

Figure 2:
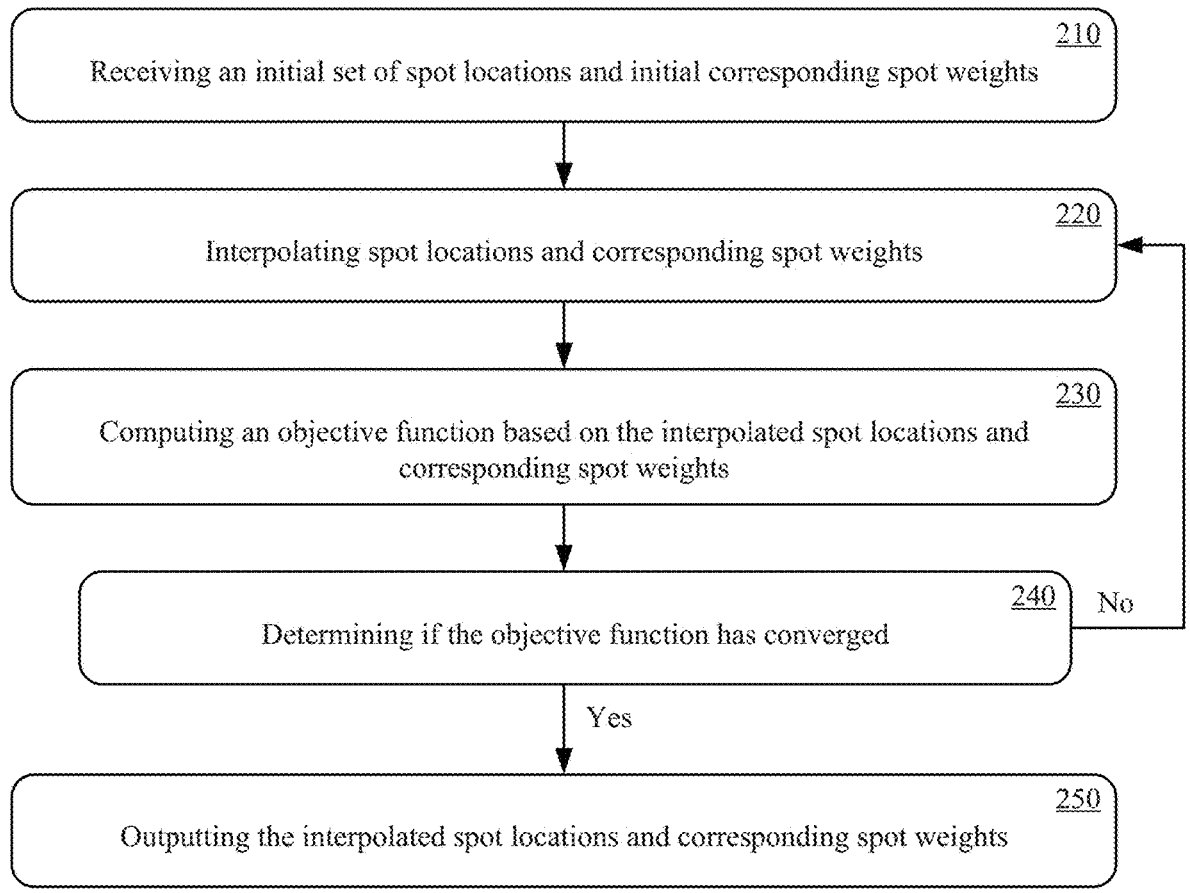
FIG. 2 shows a radiotherapy dose computation method, in accordance with aspects of the present technology.

Referring now to FIG. 2, a radiotherapy dose parameter computation method, in accordance with aspects of the present technology, is shown. The method may be implemented as computing device-executable instructions (e.g., computer program) that are stored in computing device-readable media (e.g., computer memory) and executed by a computing device (e.g., processor). In one implementation, the radiotherapy dose computation method can be utilized to optimize direct machine parameters for Intensity Modulated Proton Therapy (IMPT), Proton Modulated Arc Therapy (PMAT), Non-coplanar proton Modulated Arc Therapy (4Pi-PMAT), Ultra-High Dose Rate Radiotherapy (FLASH-RT), and the like treatment plans. The radiotherapy dose computation method can include receiving an initial set of spot locations and initial corresponding spot weights, at 210. In one implementation, an initial position and weight of spots is set by a user. For example, the spot locations can be specified by a hexagonal grid and the weights can be set to zero. In one implementation, the spot positions and spot weights are specified in two dimensions (e.g., x and y). The spot position and spot weights can be received as a dose matrix. For example, proton dose matrices can be received for proton radiotherapy treatment plans.

At 220, spot locations and corresponding spot weights are interpolated. In one implementation, the spot location and corresponding spot weights can be interpolated using nearest neighbor interpolation, bilinear interpolation, bicubic interpolation, or the like. For any spot coordinates (x, y), the dependence on the spot's position can be further specified in the dose expression according to Equation 3:

$$D_i(W, x, y) = \Sigma_{j=1}^{N} W_j \cdot IM_{ij}(x_j, y_j) \quad (3)$$

The spot dose influence matrix IM can represent a collection of individual spot doses. The evaluation of the spot dose influence matrix $IM_{i,j}(x_j, y_j)$ can be computationally expensive, as a dose calculation engine needs to be called. In contrast, interpolation of the spot dose influence matrix $IM_{i,j}(x_j, y_j)$ reduces computational workload of the radiotherapy planning system.

Figure 3:
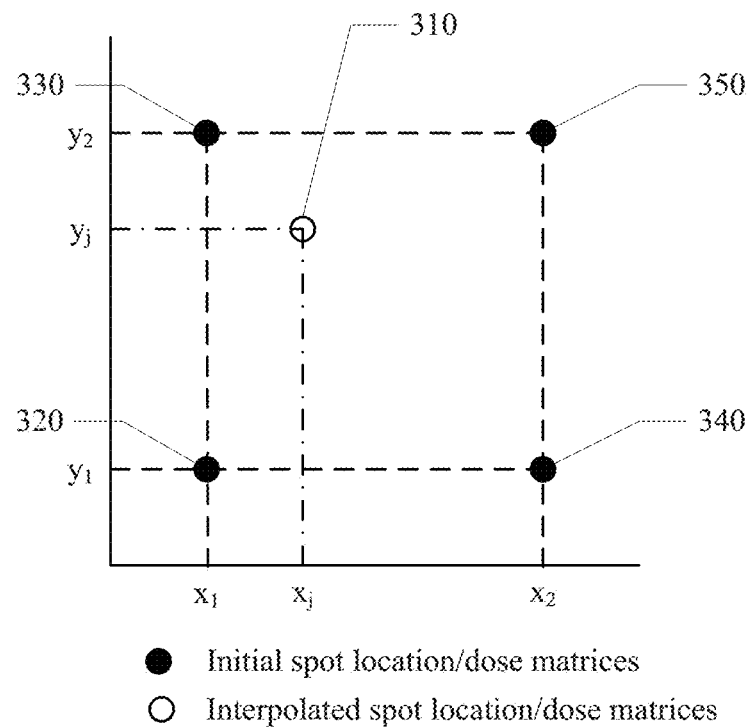
FIG. 3 illustrates spot matrix interpolation, in accordance with aspects of the present technology.

Referring now to FIG. 3, a spot matrix interpolation method, in accordance with aspects of the present technology, is illustrated. For the spot dose influence matrix $IM_{i,j}(x_j, y_j)$, the spot location at position $(x_j, y_j)$ 310 can be interpolated from its neighbor spots 320-350.

Referring again to FIG. 2, an objective function can be calculated for the interpolated spot locations and corresponding spot weights, at 230. In one implementation, an objective function $f$ that is a function of the dose D can be calculated. At 240, it is determined if the objective function converges. In one implementation, it is determined if the objective function converges when the objective function does not evolve anymore or converges to a predetermined value. If the objective function has not converged, interpolation of spot locations and corresponding spot weights and calculation of the objective function can be iteratively repeated at 220 and 230, until the iterative objective function converges.

At 250, the interpolated spot locations and corresponding spot weights can be output once the objective function converges. In one implementation, the interpolated spot locations and corresponding spot weights can be output to control a radiotherapy delivery system. Alternatively, the interpolated spot locations and corresponding spot weights can be output for storage on computing device readable media for further radiotherapy treatment plan analysis or for later use in controlling a radiotherapy delivery system.

Figure 4:
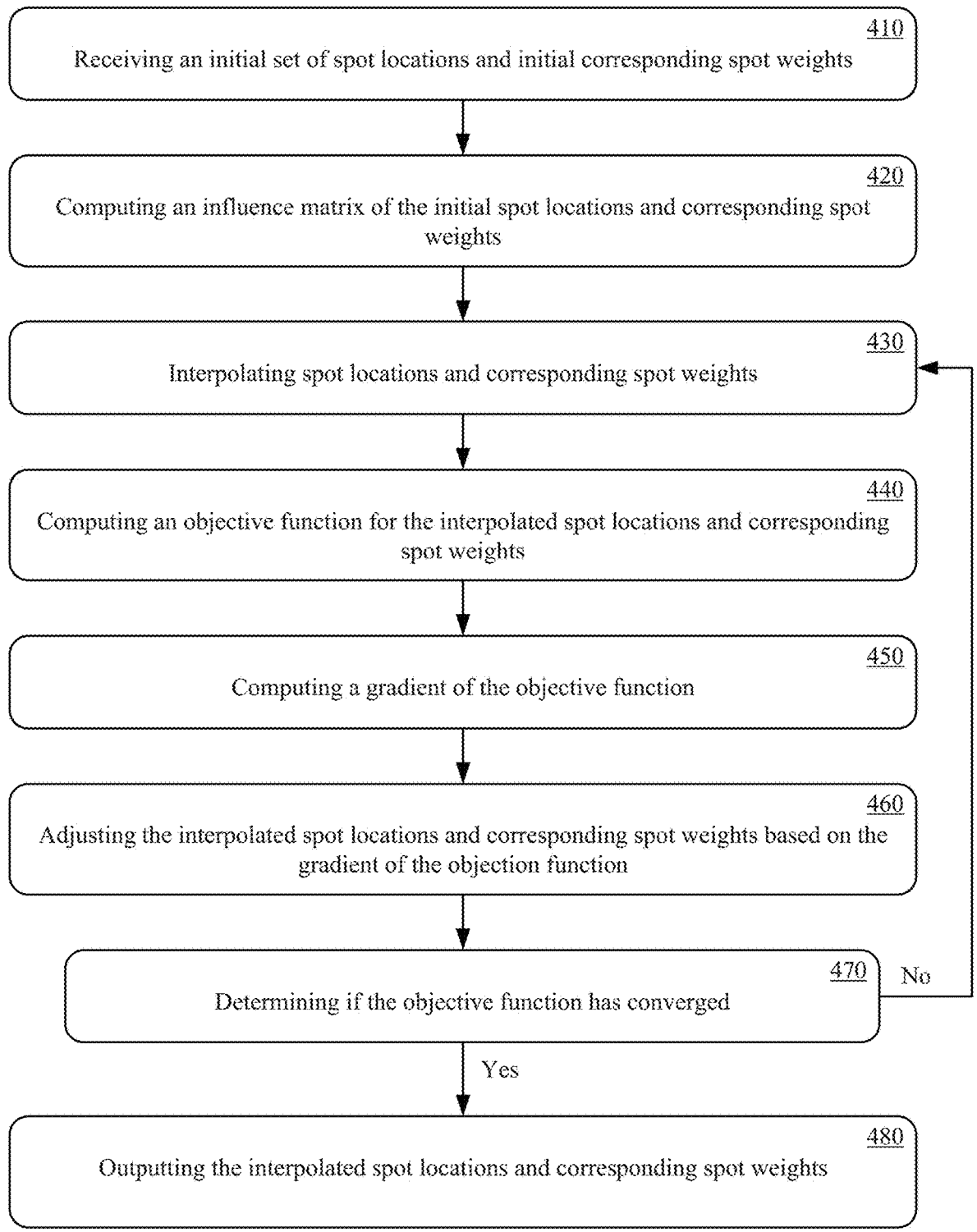
FIG. 4 shows a radiotherapy dose computation method, in accordance with aspects of the present technology.
Figures 5A, 5B, 5C, 5D:
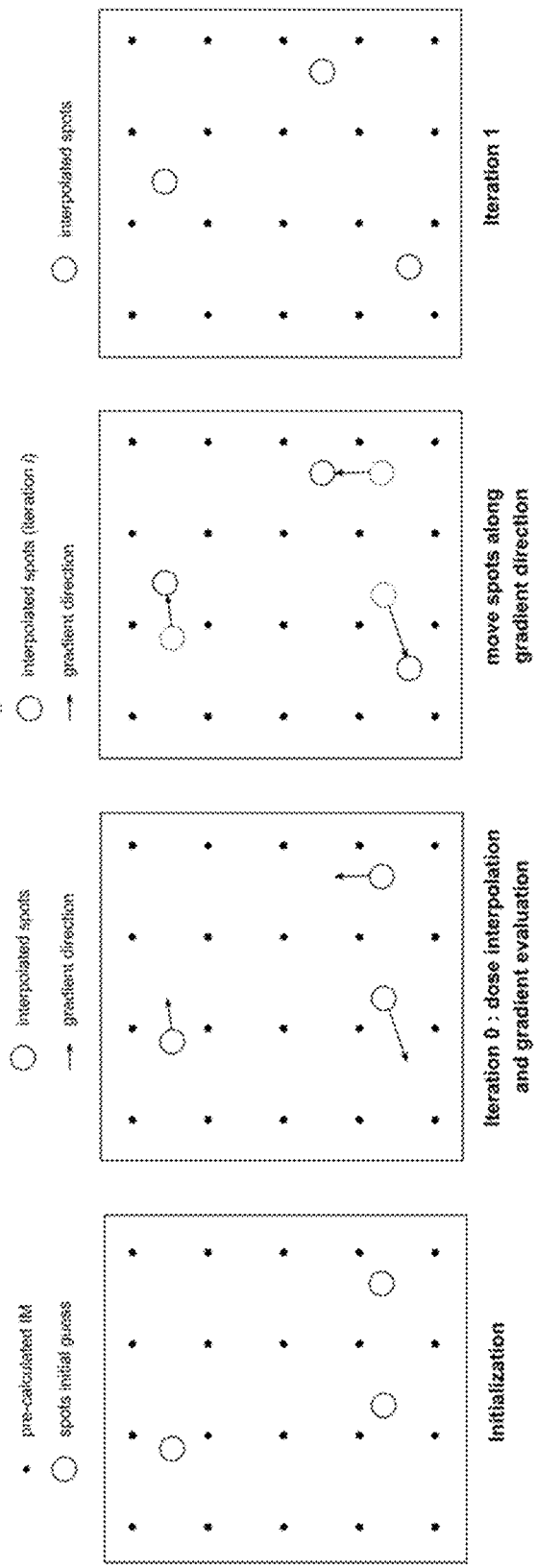
FIGS. 5A-5D illustrates spot dose and spot weight interpolation, in accordance with aspects of the present technology.

Referring now to FIG. 4, a radiotherapy dose computation method, in accordance with aspects of the present technology, is shown. The method may be implemented as computing device-executable instructions (e.g., computer program) that are stored in computing device-readable media (e.g., computer memory) and executed by a computing device (e.g., processor). In one implementation, the radiotherapy dose computation method can be utilized to optimize direct machine parameters for Intensity Modulated Proton Therapy (IMPT), Proton Modulated Arc Therapy (PMAT), Non-coplanar proton Modulated Arc Therapy (4Pi-PMAT), Ultra-High Dose Rate Radiotherapy (FLASH-RT), and the like plans. The radiotherapy dose computation method can include receiving an initial set of spot locations and initial corresponding spot weights, at 410. In one implementation, an initial position and weight of spots is set by a user. For example, the spot locations can be specified by a hexagonal grid and the weights can be set to zero. In one implementation, the spot positions and spot weights are specified in two dimensions (e.g., x and y). At 420, an initial spot dose influence matrix $IM_{i,j}(x_j, y_j)$ can be calculated. An exemplary initial influence matrix and initial spots are illustrated in FIG. 5A. As illustrated, a spot dose influence matrix based on a fixed lattice (e.g., hexagonal or rectilinear) can be precalculated. An initial guess by a user of a set of spot weight at corresponding spot locations can also be specified.

Referring again to FIG. 4, spot locations and corresponding spot weights can be interpolated, at 430. In one implementation, the spot location and corresponding spot weights can be interpolated using nearest neighbor interpolation, bilinear interpolation, bicubic interpolation, or the like. For any spot coordinates (x, y), the dependence on the spot's position can be further specified in the dose expression according to Equation 3:

$$D_i(W, x, y) = \Sigma_{j=1}^{N} W_j \cdot IM_{ij}(x_j, y_j) \quad (3)$$

Again, the evaluation of the spot dose influence matrix $IM_{i,j}(x_j, y_j)$ can be computationally expensive, as a dose calculation engine needs to be called. In contrast, interpolation of the spot dose influence matrix $IM_{i,j}(x_j, y_j)$ reduces the computational workload.

At 440, an objective function can be calculated for the interpolated spot locations and corresponding spot weights. In one implementation, the objective function $f$, that is a function of the dose D, can be calculated. At 450, a gradient of the objective function can also be calculated. In one implementation, the gradient function $\nabla f$ can have three components, the derivative along x and y positions $$\left(\frac{\partial f}{\partial x_j} \text{ and } \frac{\partial f}{\partial y_j}\right)$$

and the spot weights $$\left(\frac{\partial f}{\partial W_j}\right),$$

in accordance with equation 4:

$$\nabla f = \begin{pmatrix} \frac{\partial f}{\partial x_j} \\ \frac{\partial f}{\partial y_j} \\ \frac{\partial f}{\partial W_j} \end{pmatrix} = \frac{\partial f}{\partial D_i} \cdot \begin{pmatrix} \frac{\partial D_i}{\partial x_j} \\ \frac{\partial D_i}{\partial y_j} \\ \frac{\partial D_i}{\partial W_j} \end{pmatrix} = \frac{\partial f}{\partial D_i} \cdot \begin{pmatrix} W_j \cdot \frac{\partial IM_{ij}}{\partial x_j} \\ W_j \cdot \frac{\partial IM_{ij}}{\partial y_j} \\ IM_{ij} \end{pmatrix} \qquad (4)$$

Exemplary interpolated spots and corresponding gradients are illustrated in FIG. 5B. At 460, spot doses can be moved and their weights adjusted based on the gradient of the objective function. Exemplary spot movement based upon the corresponding gradients is illustrated in FIGS. 5C and 5D.

At 470, it is determined if the objective function converges. In one implementation, it is determined if the objective function does not evolve anymore. If the objective function has not converged, operations at 430-470 can be iteratively repeated until the iterative objective function converges.

At 480, the interpolated locations and corresponding interpolated spot weights can be output once the objective function converges. In one implementation, the interpolated locations and corresponding spot weights can be output to control a radiotherapy delivery system. Alternatively, the interpolated locations and corresponding spot weights can be output for storage on computing device readable media for further radiotherapy treatment plan analysis or for later use in controlling a radiotherapy delivery system.

Figure 6:
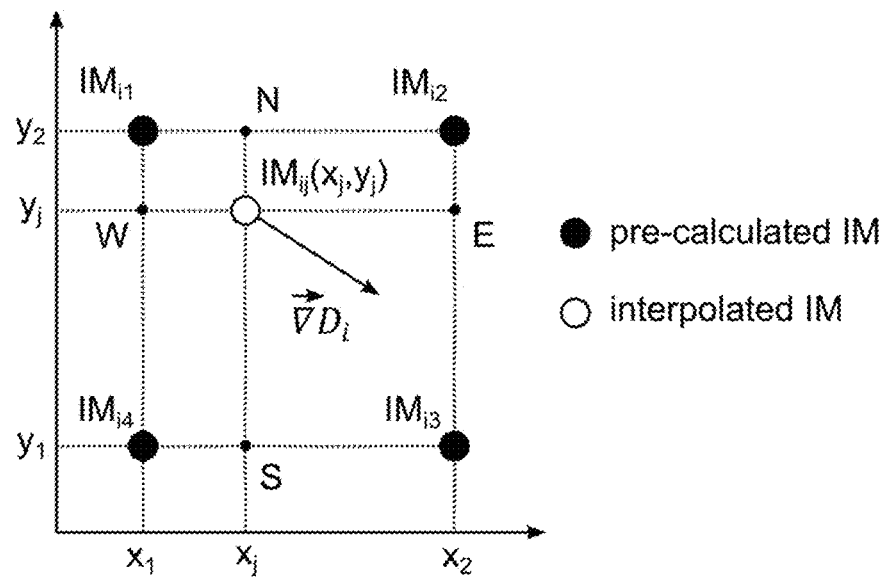
FIG. 6 illustrates spot dose and spot weight bilinear interpolation, in accordance with aspects of the present technology.

Referring now to FIG. 6, bilinear interpolation, in accordance with aspects of the present technology is illustrated. The spot dose influence matrix $IM_{i,j}(x_j, y_j)$ of a spot location at position $(x_j, y_j)$ can be approximated by a bilinear interpolation of the neighboring initial spots influence matrices.

Figure 7:
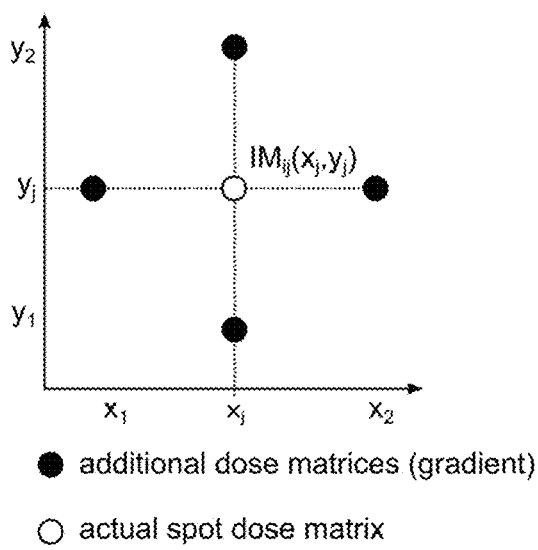
FIG. 7 illustrates a calculation of the spot dose matrix and gradient
Figure 8:
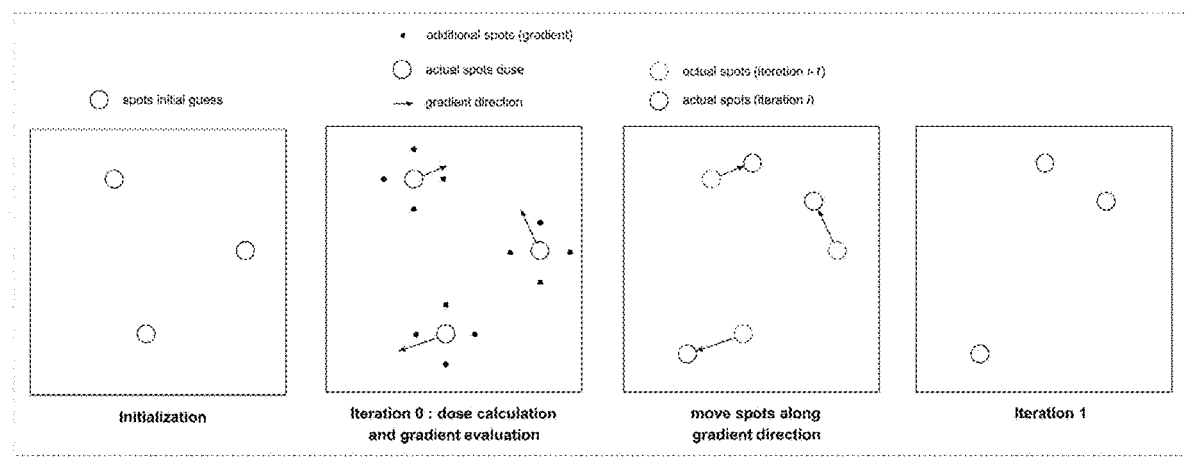
FIG. 8 illustrates spot dose and spot weight interpolation, in accordance with aspects of the present technology.

Interpolation of the spot location and corresponding spot dose can reduce the computation workload of the radiotherapy planning system as compared to exact calculation. However, if the radiotherapy planning system has sufficient computational resources, the optimal spot locations and corresponding spot doses can be calculated exactly as illustrated in FIG. 7. The gradient can be evaluated by calculating the dose of virtual spots located around the actual spot position $(x_j, y_j)$. As further illustrated in FIG. 8, the radiotherapy dose computation method can begin with an initial set of spot locations and initial corresponding spot weights. In one implementation, an initial position and weight of spots can be set by a user. The spot dose and dose distribution gradient can be computed, and then the spot locations can be moved along the gradient direction. The process can be repeated until the gradient function converges.

Figure 9:
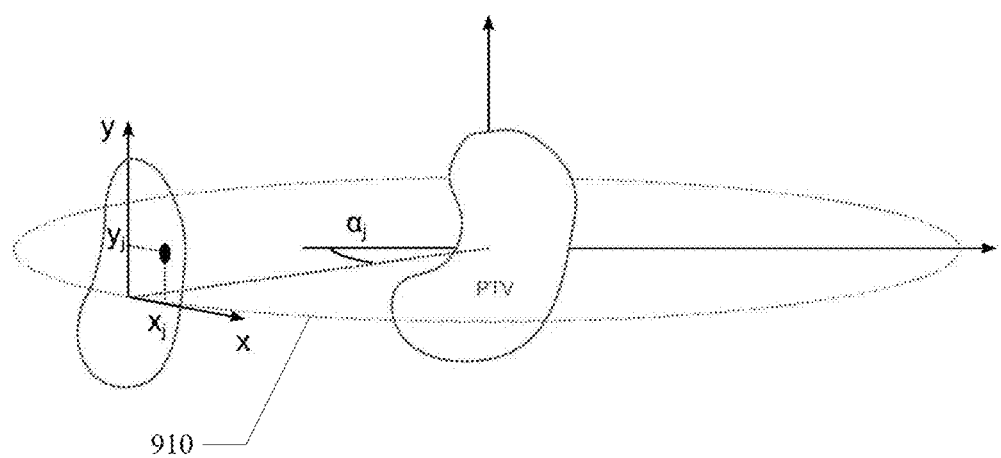
FIG. 9 illustrates an exemplary Proton Modulated Arc Therapy (PMAT) plan, in accordance with aspects of the present technology.
Figure 10:
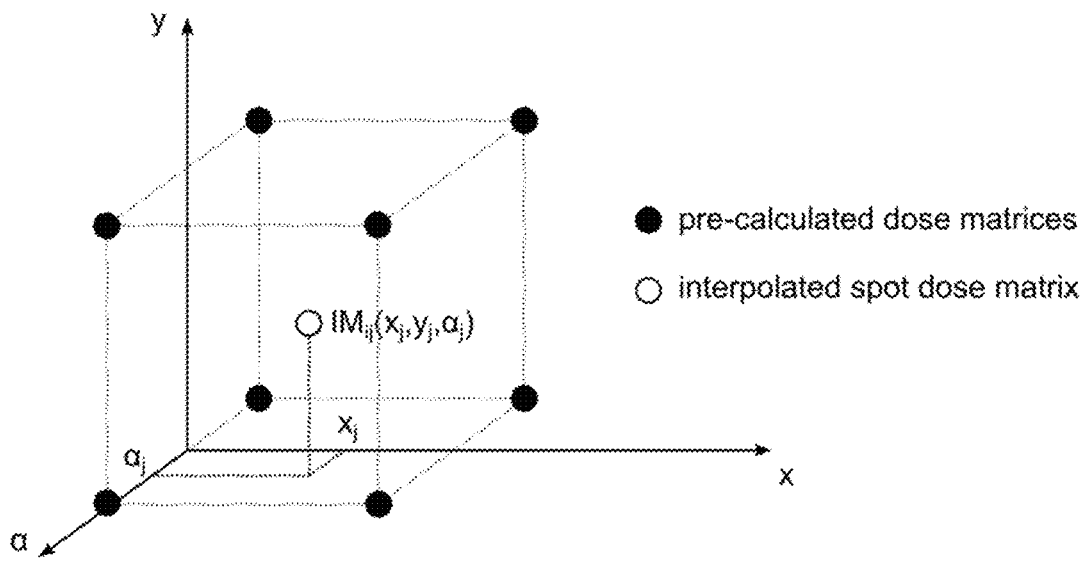
FIG. 10 illustrates spot interpolation in three dimensions, in accordance with aspects of the present technology.

Referring now to FIG. 9, an exemplary Proton Modulated Arc Therapy pan, in accordance with aspects of the present technology, is illustrated. A radiotherapy system can be configured to deliver an energy beam along an arc 910 to a planned target volume (PTV) 920. For example, a gantry can rotate about a patient on a patient table to deliver the energy beam at any angle to a cancerous region, or tumor. A scanning nozzle can further scan the energy beam about the two-dimensional projection of the planned target volume (PTV). The spot position can therefore be fully described by the three coordinates $(x_j, y_j, \alpha_j)$. Furthermore, the above-described radiotherapy parameter computation methods can be extended to three-dimensional radiotherapy treatment plans. The spot dose influence matrix $IM_{ij}(x_j, y_j, \alpha_j)$ of a spot located at position $(x_j, y_j, \alpha_j)$, can be approximated by interpolating (e.g., trilinear interpolation) the neighboring pre-calculated spot influence matrices, as illustrated in FIG. 10. For example, an initial set of spot locations and initial corresponding spot weights can be received, at 410. In one implementation, an initial positions and weights of spots are set by a user. For example, the spot locations can be specified by a hexagonal grid and the weights can be set to zero. At 420, an initial influence matrix $IM_{ij}(x_j, y_j, \alpha_j)$ can be calculated for a plurality of different sub-arcs.

At 430, spot locations and corresponding spot weights can be interpolated. In one implementation, the spot location and corresponding spot weights can be interpolated using nearest neighbor interpolation, bilinear interpolation, trilinear interpolation bicubic interpolation, or the like. For any spot coordinate $(x, y, \alpha_j)$, the dependence on the spot's position can be further specified in the dose expression according to Equation 9:

$$D_i(W,x,y,\alpha_j) = \Sigma_{j=1}^{N} W_j \cdot IM_{ij}(x_j, y_j, \alpha_j) \qquad (9)$$

Again, the evaluation of the spot dose influence matrix $IM_{i,j}(x_j, y_j, \alpha_j)$ can be computationally expensive, as a dose calculation engine needs to be called. In contrast, interpolation of the influence matrix $IM_{i,j}(x_j, y_j, \alpha_j)$ reduces computational workload. However, if the radiotherapy planning system has sufficient computational resources, the exact spot locations and corresponding spot doses can be calculated.

At 440, an objective function can be calculated for the interpolated spot locations and corresponding spot weights. In one implementation, the objective function $f$, that is a function of the dose D, can be calculated. At 450, a gradient of the objective function can also be calculated. In one implementation, the gradient function $\nabla f$ can have three components, the derivative along x and y positions $$\left(\frac{\partial f}{\partial x_j} \text{ and } \frac{\partial f}{\partial y_j}\right)$$

and the spot weights $$\left(\frac{\partial f}{\partial W_j}\right).$$

At 460, spot positions can be moved and their weights adjusted based on the gradient of the objective function.

At 470, it is determined if the objective function converges. In one implementation, it is determined if the objective function converges when the objective function does not evolve anymore or converges to a predetermined value. If the objective function has not converged, operations at 430-470 can be iteratively repeated until the iterative objective function converges.

At 480, the interpolated locations and corresponding spot weights can be output once the objective function converges. In one implementation, the interpolated locations and corresponding spot weights can be output to control a radiotherapy delivery system. Alternatively, the interpolated locations and corresponding spot weights can be output for storage on computing device readable media for further radiotherapy treatment plan analysis or for later use in controlling a radiotherapy delivery system.

Referring now to FIG. 10, spot interpolation in three dimensions, in accordance with aspects of the present technology, is illustrated. As illustrated the influence matrix $IM_{i,j}(x_j, y_j, \alpha_j)$ for the spot location at position $(x, y, \alpha_j)$ can be interpolated from its neighbor spots.

Figure 11:
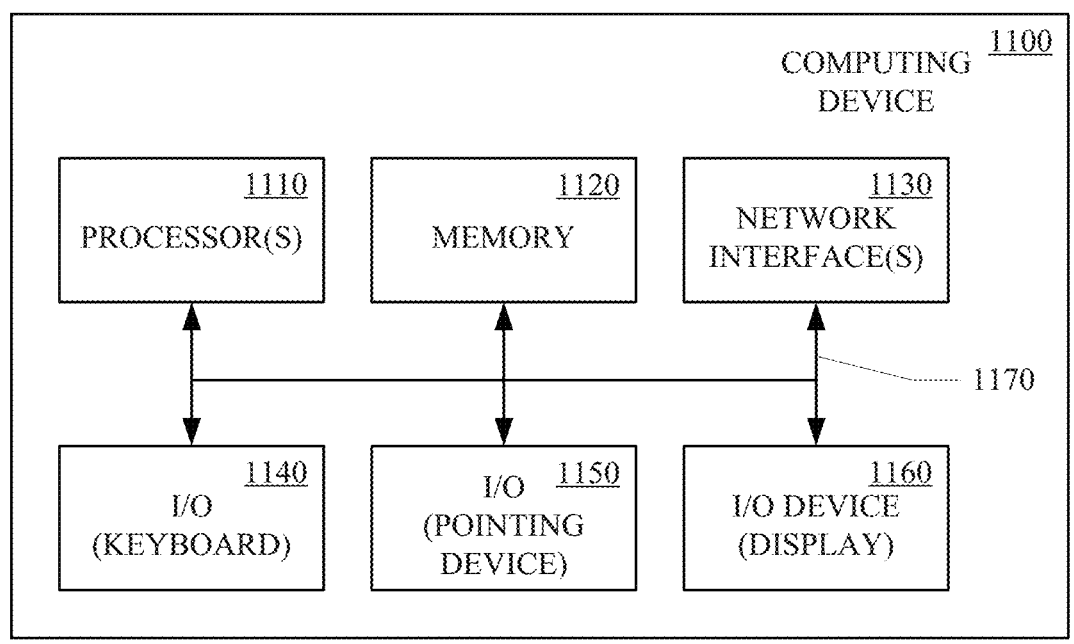
FIG. 11 shows an exemplary computing device for implementing one or more aspects of the present technology.

Referring now to FIG. 11, a computing device for implementing one or more aspects of the present technology is shown. The computing device 1100 can include one or more processors 1110, one or more memories 1120, one or more network interface 1130, and one or more input/output devices 1140-1160 such as keyboards, pointing devices, displays and/or the like, coupled together by one or more busses 1170. The computing device 1100 can be any type of computing device, including but not limited to embedded processors, desktop Personal Computers (PCs), laptop PCs, server computer, virtual machine, cloud computing platform, or the like. One or more software routines (e.g., computing device executable instructions) stored in the one or more memories (e.g., computing device readable media) 1120, when executed by the one or more processors 1110, can implement the radiotherapy dose computation systems and methods as described above.

Aspects of the present technology can advantageously provide direct machine parameter optimization for radiotherapy treatment techniques such as, but not limited to, Intensity Modulated Proton Therapy (IMPT), Proton Modulated Arc Therapy (PMAT), Non-coplanar proton Modulated Arc Therapy (4Pi-PMAT), Ultra-High Dose Rate Radiotherapy (FLASH-RT). Aspects of the present invention can optimize the dose as a function of both the spot weight and the spot position. Aspects of the present invention can advantageously be utilized to find optimal solutions for spot weight limited applications, to overcome machine hardware constraints, to increase the dose rate (e.g., FLASH-RT), to reduce the number of spots in a treatment plan, to reduce delivery times, and/or the like. Aspects of the present technology can provide dose optimizations that are as good or better as compared to optimizing just the spot weights utilizing fixed spot locations Dose optimization based on both spot weight and spot location utilizing interpolation can also advantageously reduce computation workload, as compared to directly computing spot weights and spot locations.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A radiotherapy dose computation method comprising:
   receiving an initial set of spot locations and initial corresponding spot weights;
   computing a spot dose influence matrix of the initial spot locations and corresponding spot weights;
   interpolating spot locations and corresponding spot weights;
   computing an objective function for the interpolated spot locations and corresponding spot weights;
   computing a gradient of the objective function;
   adjusting the interpolated spot locations and corresponding spot weights based on the gradient of the objective function;
   determining if the objective function converges;
   iteratively interpolating the spot locations and corresponding spot weights, computing the objective function, computing the gradient, and adjusting the interpolated spot locations and corresponding spot weights until the objective function converges; and
   outputting the interpolated spot locations and corresponding spot weights when the objective function converges.

2. The radiotherapy dose computation method of claim 1, wherein received initial set of spot locations and initial corresponding spot weights comprises a dose matrix.

3. The radiotherapy dose computation method of claim 2, wherein the dose matrix comprises a proton dose matrix.

4. The radiotherapy dose computation method of claim 1, wherein the spot locations and corresponding spot weights are interpolated using nearest neighbor interpolation.

5. The radiotherapy dose computation method of claim 1, wherein the spot locations and corresponding spot weights are interpolated using bilinear interpolation.

6. The radiotherapy dose computation method of claim 1, wherein the spot locations and corresponding spot weights are interpolated using bicubic interpolation.

7. The radiotherapy dose computation method of claim 1, wherein the spot locations and corresponding spot weights are interpolated using trilinear interpolation.

8. The radiotherapy dose computation method of claim 1, wherein the spot locations comprise two coordinate parameters $(x, y)$.

9. The radiotherapy dose computation method of claim 1, wherein the spot locations comprise three coordinate parameters $(x, y, \alpha)$.

10. The radiotherapy dose computation method of claim 1, wherein the initial set of spot locations and initial corresponding spot weights are set by a user.

11. The radiotherapy dose computation method of claim 10, wherein the initial spot locations are specified based on a hexagonal or rectilinear grid and the initial corresponding spot weights are set to a zero value.

12. One or more computing device readable media storing instructions that when executed by one or more processing units perform a radiotherapy dose computation method comprising:
   receiving an initial set of spot locations and initial corresponding spot weights;
   computing a spot dose influence matrix of the initial spot locations and corresponding spot weights;
   interpolating spot locations and corresponding spot weights;
   computing an objective function for the interpolated spot locations and corresponding spot weights;
   computing a gradient of the objective function;
   adjusting the interpolated spot locations and corresponding spot weights based on the gradient of the objective function;
   determining if the objective function converges;
   iteratively interpolating the spot locations and corresponding spot weights, computing the gradient, and adjusting the interpolated spot locations and corresponding spot weights until the objective function converges; and
   outputting the interpolated spot locations and corresponding spot weights when the objective function converges.

13. The one or more computing device readable media storing the instructions that when executed by the one or more processing units perform the radiotherapy dose computation method of claim 12, wherein the interpolated spot locations and corresponding spot weights are output to a radiotherapy delivery system selected from the group consisting of an Intensity Modulated Proton Therapy (IMPT) delivery system, a Proton Modulated Arc Therapy (PMAT) delivery system, a Non-coplanar proton Modulated Arc Therapy (4Pi-PMAT) delivery system, and an Ultra-High Dose Rate Radiotherapy (FLASH-RT) delivery system.

14. The one or more computing device readable media storing the instructions that when executed by the one or more processing units perform the radiotherapy dose computation method of claim 12, wherein the spot locations are interpolated as a function of two coordinate parameters (x, y).

15. The one or more computing device readable media storing the instructions that when executed by the one or more processing units perform the radiotherapy dose computation method of claim 12, wherein the spot locations are interpolated as a function of three coordinate parameters (x, y, $\alpha$).

16. The one or more computing device readable media storing the instructions that when executed by the one or more processing units perform the radiotherapy dose computation method of claim 12, wherein the spot locations and corresponding spot weights are interpolated using nearest neighbor interpolation, bilinear interpolation, bicubic interpolation or trilinear interpolation.

17. A radiotherapy dose computation method comprising:
   receiving a set of spot locations and corresponding spot weights;
   interpolating the set of spot locations and corresponding spot weights as a function of two coordinate location parameters (x, y);
   computing a gradient function of the interpolated spot locations and corresponding spot weights;
   iteratively interpolating the spot locations, the corresponding spot weights and gradient function until the gradient function converges; and
   controlling a radio therapy delivery system based on the interpolated spot locations and corresponding spot weights once the gradient function converges.

18. The radiotherapy dose computation method of claim 17, further comprising interpolating the set of spot locations and corresponding spot weights as a function of three coordinate location parameters (x, y, $\alpha$).

19. The radiotherapy dose computation method of claim 17, wherein the spot locations and corresponding spot weights are interpolated using nearest neighbor interpolation, bilinear interpolation, bicubic interpolation or trilinear interpolation.

20. The radiotherapy dose computation method of claim 17, wherein the radio therapy delivery system comprises an Intensity Modulated Proton Therapy (IMPT) delivery system, a Proton Modulated Arc Therapy (PMAT) delivery system, a non-coplanar proton Modulated Arc Therapy (4Pi-PMAT) delivery system, and an Ultra-High Dose Rate Radiotherapy (FLASH-RT) delivery system.

* * * * *